US010751343B2

(12) United States Patent
Merkus et al.

(10) Patent No.: US 10,751,343 B2
(45) Date of Patent: Aug. 25, 2020

(54) NASAL COMPOSITIONS STIMULATING CILIARY ACTIVITY

(71) Applicants: Innotesto BVBA, Kasterlee (BE); Veramed BV, Laren (NL)

(72) Inventors: Franciscus Wilhelmus Henricus Maria Merkus, Kasterlee (BE); Bart Merkus, Laren (NL)

(73) Assignees: Innotesto BVBA, Kasterlee (BE); Veramed BV, Laren (NL)

( * ) Notice: Subject to any disclaimer, the term of this patent is extended or adjusted under 35 U.S.C. 154(b) by 0 days.

(21) Appl. No.: 16/690,821

(22) Filed: Nov. 21, 2019

(65) Prior Publication Data

US 2020/0085831 A1    Mar. 19, 2020

Related U.S. Application Data

(62) Division of application No. 15/031,939, filed as application No. PCT/EP2014/073400 on Oct. 30, 2014, now abandoned.

(30) Foreign Application Priority Data

Oct. 31, 2013   (NL) ..................................... 1040474

(51) Int. Cl.
*A61K 31/522* (2006.01)
*A61K 9/00* (2006.01)
(Continued)

(52) U.S. Cl.
CPC .......... *A61K 31/522* (2013.01); *A61K 9/0043* (2013.01); *A61K 9/08* (2013.01); *A61K 47/02* (2013.01)

(58) Field of Classification Search
CPC .... A61K 31/522; A61K 9/0043; A61K 47/02; A61K 9/08
See application file for complete search history.

(56) References Cited

U.S. PATENT DOCUMENTS 4,689,223 A * 8/1987 Arias ..................... A61K 33/06
                                                          424/682
4,778,810 A   10/1988 Wenig et al.
(Continued)

FOREIGN PATENT DOCUMENTS

JP    2001302518 A   10/2001
JP    2003128537 A    5/2003
(Continued)

OTHER PUBLICATIONS

Chatterjee et al., J Indian Soc Periodontol. Apr.-Jun. 2012; 16(2): 161-167 (Year: 2012).*
(Continued)

*Primary Examiner* — San Ming R Hui
(74) *Attorney, Agent, or Firm* — Dinsmore & Shohl, LLP

(57) ABSTRACT

Nasal compositions, comprising an aqueous solution containing caffeine and/or theobromine in a total concentration of up to about 0.5 percent (w/v) and an aqueous carrier having a pH of about 6-8 and comprising physiologically acceptable salts of sodium, potassium and calcium. The nasal composition when used as a nasal spray or as nasal drops or irrigation fluid is able to clean the nasal passages and to stimulate nasal mucociliary clearance and, in contrast to nasal decongestants, may be used on a daily-basis for a period longer than 5 days.

20 Claims, 1 Drawing Sheet

(51) Int. Cl.
*A61K 47/02* (2006.01)
*A61K 9/08* (2006.01)

(56) References Cited

U.S. PATENT DOCUMENTS

| | | | |
|---|---|---|---|
| 5,169,849 | A | 12/1992 | Kiechel et al. |
| 5,508,282 | A | 4/1996 | Tulin-Silver et al. |
| 5,605,892 | A | 2/1997 | Ikejiri et al. |
| 6,166,025 | A | 12/2000 | Harding |
| 7,166,435 | B2 * | 1/2007 | Rosenbloom ........ A61K 9/0043 435/6.14 |
| 7,541,052 | B1 | 6/2009 | Cordray |
| 8,221,798 | B1 | 7/2012 | Abidin |
| 2003/0180380 | A1 | 9/2003 | Hansen |
| 2011/0086114 | A1 | 4/2011 | Zinreich et al. |

FOREIGN PATENT DOCUMENTS

| | | | |
|---|---|---|---|
| JP | 2003128549 A | | 5/2003 |
| JP | 2003128552 A | | 5/2003 |
| WO | 8804929 A1 | | 7/1988 |
| WO | WO9842322 A2 | | 10/1998 |
| WO | WO0100218 A1 | | 1/2001 |
| WO | WO2015063239 A1 | | 5/2015 |

OTHER PUBLICATIONS

Mallants et al., "Effect of preservatives on ciliary beat frequency in human nasal epithelial cell culture: Single versus multiple exposure", International Journal of Pharmaceutics 338, 2007, pp. 64-69.
CFR—Code of Federal Regulations Title 21; source: www.accessdata.fda.gov/sodium benzoate 184.1733 (accessed Aug. 30, 2016).
Mathé et al, "From Fernand Widal rhinitis syndrome and chronic sinusitis to total muco-ciliary disease", Biomed Pharmacother, 1988, 42(8), 489-92, France, Abstract.
Nawrot et al., "Effects of Caffeine on human health", Food Additives and Contaminants, 2003, vol. 20, No. 1, 1-30.
Joris et al., "Elemental Composition of Human Airway Surface Fluid in Healthy and Diseased Airways", Am Rev Respir Dis, vol. 148, 1993, pp. 1633-1637.
Braiman et al., "Purinergic Stimulation of Ciliary Activity", Drug Development Research, 2000, 50:550-554.
Xylometazoline Nasal, source 2012: emedicinehealth.com, pp. 1-3.
International Search Report completed Jan. 7, 2015 pertaining to PCT/EP2014/073400 filed Oct. 30, 2014.
Oliveira et al., Cienc. Tecnol. Aliment., Campinas, 32(1):163-166, Jan.-Mar. 2012.

* cited by examiner

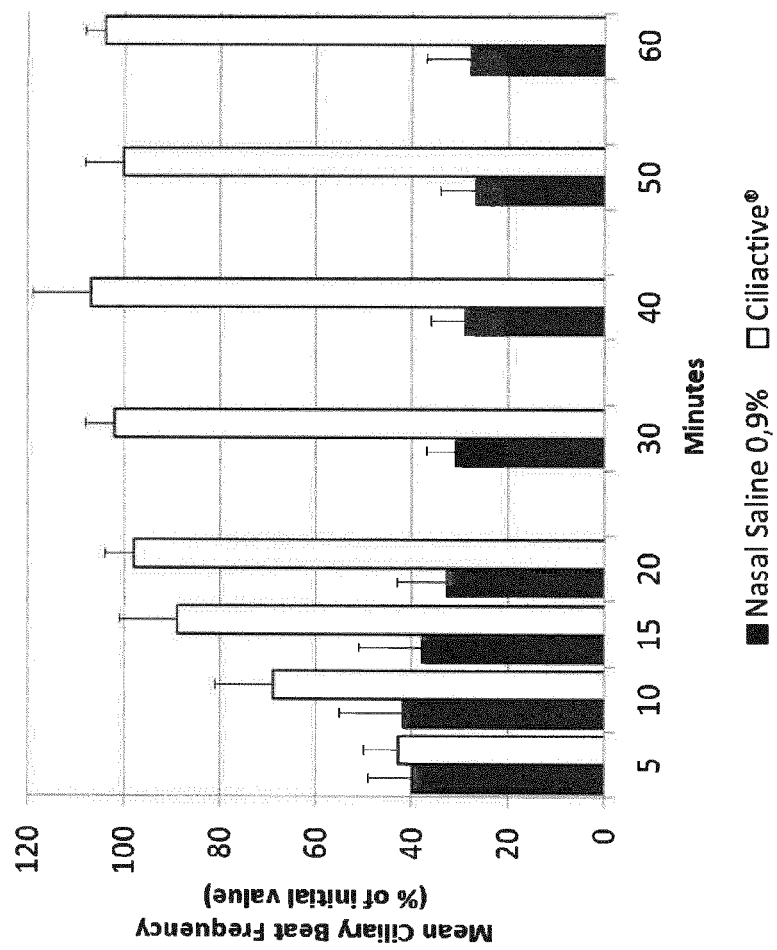

NASAL COMPOSITIONS STIMULATING CILIARY ACTIVITY

CROSS REFERENCE TO RELATED APPLICATIONS

This application is a division of U.S. application Ser. No. 15/031,939, filed Apr. 25, 2016, which is a U.S. National Stage Entry under 35 U.S.C. § 371 of PCT/EP2014/073400, filed on Oct. 30, 2014, which claims priority to NL 1040474 filed Oct. 31, 2013, the contents of which are hereby incorporated by reference in their entirety.

FIELD OF THE PRESENT DISCLOSURE

The present disclosure relates to nasal medications including nasal sprays, drops and irrigation fluids or washes, and provides aqueous nasal compositions comprising one or more agents and excipients in an amount sufficient to stimulate ciliary movement and nasal mucociliary clearance. These medications are able to remove noxious materials from the nose to prevent viral, bacterial and allergic diseases in the upper airways. They can be used on a daily basis and for a long period of time (longer than about 3-5 days) to treat or prevent nasal congestion and nasal allergic and infectious diseases, or to clean the nose.

BACKGROUND INFORMATION

The main function of the nose is to warm, filter and moisturize incoming air. Nasal passages are lined with an epithelial cell layer called nasal mucosa, composed of different cell types. Some cells secrete a gel-like substance called mucus, composed mainly of water, and very small amount is of mucin and inorganic salts. The mucus layer functions as a trap for all noxious substances entering the nose such as dust, bacteria, and viruses.

Mucus is cleared from the nose by millions of cilia on top of the ciliated columnar cells in the nasal mucosa. These cilia "sweep" mucus and trapped material through the nasal passages in the direction of the back of the throat where it is swallowed. This line of defense, protecting the human body against all noxious material (bacteria, allergens, and viruses) entering the nose, is called nasal mucociliary clearance. Impairment of the nasal mucociliary clearance results in diseases of the upper airways. Therefore, it may be advantageous to stimulate nasal mucociliary clearance by a nasal medication and activate the natural defense mechanism of the nose to prevent viral, bacterial or allergic diseases. Such a nasal medication may clean the nasal passages and offer relief and defense against infectious and allergic diseases.

Normal nasal mucociliary transit time (also called Mucus Transit Time, MTT) in humans has been reported to be about 15-20 min. Transit times of more than 30 min are considered to be abnormal, and are an indication of impaired mucociliary clearance. The average rate of nasal clearance is about 8 mm/min, ranging from less than 1 to more than 20 mm/min. It has been demonstrated with nasal sprays containing a radiolabeled compound, that clearance takes place in two phases. The first phase lasts about 15-20 min, in which the major part of the administered dose is cleared from the ciliated nasal respiratory mucosa. The second clearance phase is slower, and removes the part of the nasal medication that is deposited on the non-ciliated vestibule and anterior septal area in the nose. The first phase dominates the clearance of allergens, bacteria and viruses from the major respiratory passages in the nose.

A simple and inexpensive method for estimating the mucociliary clearance and the MTT in vivo is by using dyes as a marker. Drops or particles coloured by a strong dye are placed into the anterior part of the nasal cavity. The time for the dye to appear in the pharyngeal cavity is measured by monitoring its appearance in the pharyngeal cavity. Regular inspection is needed. Another method uses a sweet-tasting particle, usually saccharin, deposited in the anterior part of the nasal cavity. The time between deposition and sensation of a sweet taste is taken as the MTT. A disadvantage of the saccharin test is that some subjects have a high taste threshold or do not taste the saccharin properly. Also, it is not possible to do several saccharin tests in a short period of time, because the taste of saccharin takes hours to disappear completely. To compensate for the disadvantages of both methods, a combination of a dye and saccharin may be used.

Most nasal products on the market are used to treat nasal congestion (stuffy nose). The nose gets congested (stuffy) when the nasal epithelial tissue and the blood vessels are inflamed and swollen. Nasal congestion can interfere with the ears, hearing, speech development and sleep. A stuffy nose is usually caused by a virus or bacteria. Causes include a common cold, influenza, sinus infection, also allergies such as hay fever, nasal polyps and vasomotor rhinitis. Nasal decongestants are widely used. However, a so-called rebound nasal congestion occurs in patients taking nasal decongestants, like oxymetazoline, more than twice daily and for more than 3-5 consecutive days. This indicates that there is a strong medical need to treat nasal congestion and nasal infections with a medication that is free from decongestants and a medication that can be used for a longer period than 3-5 days, and preferably longer than 5 days.

Also, it has been proven that nasal saline solutions, widely used by millions of patients, often impair the ciliary activity, and consequently reduce the nasal mucociliary clearance and increase nasal MTT. Also many nasal products on the market contain preservatives which are not only rather toxic but also responsible for a serious reduction of the ciliary activity.

Accordingly, a medical need exists for nasal medications including sprays and drops, preferably without preservatives, providing aqueous nasal compositions comprising one or more agents and excipients in an amount sufficient to (1) stimulate ciliary movement and nasal mucociliary clearance and (2) decrease the nasal mucus transit time (3) remove noxious materials as soon as possible to prevent viral, bacterial and allergenic diseases in the upper airways. Also there is a need for a nasal medication that (4) can be used for a longer period of time (longer than 3-5 days) to treat or prevent nasal congestion.

During investigations carried out by the applicant on ciliated cells exposed to sodium chloride solution (NaCl 0.9 percent w/v in water, also called saline), the ciliary beat frequency (CBF) was found to increase after the addition of small amounts of potassium chloride, calcium chloride and water, optionally together with small amounts of sodium bicarbonate and glucose. The CBF of ciliated human nasal and chicken tracheal tissue was also surprisingly found to remain constant over many hours in isotonic solutions containing a combination of sodium, potassium and calcium chloride salts; while in solutions containing only NaCl (0.9 percent) the CBF decreased to 50-70 percent of the initial value within 1-2 hours. This indicates that the presence of sodium, potassium and calcium ions in specific concentrations is necessary for stimulation/activation of the ciliary movement and optimal functioning of the mucociliary clearance in the nose. The presence of these salts is especially required when nasal compositions are used on a daily basis for weeks. Supportive evidence for the specific function of these ions can be found in the literature, for instance "Ca-ions in mucociliary tissue of higher organisms are essential for ciliary beating, with a rise in intracellular Ca-ions correlating with a rise in ciliary beat frequency" (Braiman et al, Purinergic stimulation of ciliary activity, Drug Development Research 2000; 50:550-554).

Further investigations (see under Experimental Section) on chicken embryo ciliated tissue and on human nasal ciliated cell cultures surprisingly demonstrated that xanthine derivates in small amounts increased the CBF for a long time. Compositions, called Ciliactive®, were prepared by adding a xanthine derivative such as caffeine and/or theobromine (up to 0.5 percent w/v) to aqueous isotonic solutions, comprising sodium chloride and small amounts of potassium chloride and calcium chloride. Cilia experiments using human ciliated cell cultures with these Ciliactive® solutions showed a very significant increase in ciliary beat frequency (CBF) in comparison with the CBF measured after exposure of the ciliated cells to caffeine-free saline or culture medium solutions. The caffeine in the Ciliactive® solution thus acts synergistically with the salt component (sodium-potassium-calcium salts) to achieve a strong and long-lasting effect on the CBF. Ciliactive® may be used daily for weeks or months without the depletion of important ions in the nasal mucosa, and is a highly effective longterm medication for the treatment or prevention of nasal congestion or nasal allergic or infectious diseases, or for nasal cleansing.

Compared with the effect of saline, the increase of CBF under the influence of Ciliactive® was very statistically significant after 5 hours, also after 24 hours, and also after 48 hours, with p-values of respectively 0.003, 0.001 and 0.005. As a result, it may be concluded that solutions containing caffeine and also sodium chloride, potassium chloride and calcium chloride stimulate mucociliary clearance in the human nose, because ciliary movement is the driving force of mucociliary clearance in the human nose.

Certain known nasal products contain caffeine. U.S. Pat. No. 5,169,849 (Kiechel et al.) discloses a liquid nasal pharmaceutical composition which contains the antimigraine drug dihydroergotamine which is capable of depressing ciliary function and an effective amount of a xanthine, for instance caffeine, which is capable of increasing the ciliary function again over a period of 20 minutes after application of the antimigraine drug and the xanthine in a nasal spray. The purposes of the xanthine is to counteract the depressive effect of the antimigraine drug on CBF following administration. The weight ratio of the dihydroergotamine to the xanthine is from 0.1:1 to 10:1.

U.S. Pat. No. 5,508,282 teaches a nasal composition and method for treating acute or chronic rhinosinusitis containing caffeine. The active substance caffeine is "employed as a topical vasoconstrictor" (column 3 line 57-58). The preferred amount of caffeine is 1.7 percent (17 mg/ml) and the contemplated range is 5-100 mg/ml (column 3, line 63-64). According to "the most preferred embodiment of the present disclosure" the formulation contains also benzoic acid or sodium benzoate 17 mg/ml" (column 4, lines 5-35), in a similar amount as caffeine. However, such a combination as proposed by U.S. Pat. No. 5,508,282 is not advantageous from a scientific point of view. The Pharmaceutical Codex, 12th edition teaches that sodium benzoate (and/or benzoic acid) is a solubilizer for caffeine, because it builds a complex with caffeine. Caffeine itself is not soluble in water at room temperature in a concentration above 16 mg/ml (The Pharmaceutical Codex, W. Lund, Editor, 12th edition, The Pharmaceutical Press, London 1994, pp 771-772). Also, sodium benzoate is a preservative. From the literature it is known that preservatives inhibit nasal ciliary movement and therefore the use of sodium benzoate may be harmful (e.g. Mallants R et al, Effect of preservatives on ciliary beat frequency in human nasal epithelial cell culture; single and multiple exposure, Int. J. Pharmaceutics 2007; 338:64-69). Further, the FDA only considers sodium benzoate as a safe excipient in food when the concentration is limited to 0.1 percent by weight and in U.S. Pat. No. 5,508,282 the preferred concentration of sodium benzoate is higher (source:www.accessdata.fda.gov/sodium benzoate 184.1733)

One of the methylxanthines, theophylline, is a drug mainly used as an asthma medicine and prescribed as tablet or oral syrup to facilitate mucociliary clearance. G. Mathe et al. (Biomed. Pharmacotherapy 1988; 42:489-492) teach that acid air pollution may play a part in the mucus cilia transport syndrome, as the respiratory mucus does not tolerate an acid pH. Their advice is to apply alkaline aerosols and also to use theophyllin because it "activates cilia mobility, usually increase mucus fluidity and facilitate its clearance from the sinuses".

US2011/086114 describes nasal compositions for moisturizing nasal passages and for stimulating mucous transport by increasing ciliary beat frequency, comprising Ascorbic acid (Vitamin C), but not caffeine or theobromine.

WO98/42322 teaches that theobromine can be used as an antitussive agent because it stimulates mucociliary clearance, and discloses for instance a solution of theobromine 25 percent (w/w) in an oral syrup with 30 percent (w/w) saccharose in water to alleviate irritable cough.

Several patent applications disclose compositions for administration on the mucous membranes comprising amounts of a xanthine derivative. For instance, caffeine to improve the sense of a refrigerant (e.g. menthol) on a mucous membrane (JP2001 302518) or caffeine, theophylline or the like to stabilize an azulene derivative in an aqueous composition (JP2003 128537). The stability of vitamin E is improved by including a xanthine (caffeine and others) in the compositions for mucous membranes (JP2003 128552), and similarly also the stability of chlorpheniramine and its salts is improved when compounded with a xanthine like caffeine (JP2003 128549).

Also others have proposed caffeine in a nasal medication. U.S. Pat. No. 4,778,810 teaches the use of a nasal medication wherein caffeine is used as the only therapeutically active ingredient, in an extreme high dose, and used for its central stimulating effect. The concentration described is 25 mg/ml to 2000 mg/ml. Also on the internet a caffeine energy nasal spray (called "Turbo snort") is promoted containing about 1 percent caffeine (10 mg/ml of caffeine), providing for instance 4 sprays of in total 0.365 ml, containing about 4 mg of caffeine. Suggested use is to increase energy, alertness and performance. The solution contains not only caffeine but also creatine, taurine, glutamine, ascorbic acid, water, and glycerin (www.turbosnort.com).

Several medications comprising inorganic salt compositions have been disclosed to treat rhinitis and other nasal symptoms. U.S. Pat. No. 7,541,052 discloses a method of treating a patient suffering from inflammation and/or irritation of the nasal passageways which comprises nasally administering an aqueous hypertonic composition consisting essentially of about 1 to 10 percent by weight of salts consisting essentially of: A) 1) about 45 to 60 percent by weight of magnesium chloride; 2) about 29 to 40 percent by weight of potassium chloride, and 3) about 0.4 to 5 percent by weight of salts selected from the group consisting of magnesium bromide, calcium chloride, calcium bromide, sodium bromide and magnesium sulfate, and B) the remainder being water, whereby mucus secretion is induced and the irritation or inflammation is reduced.

WO01/00218 discloses a similar composition in water, consisting essentially of about 0.5 to 5 percent by weight of a Dead Sea salt and mineral composition, including about 31-35 percent magnesium halide, 24-26 percent potassium halide, 4-8 percent sodium halide, 0.4-0.6 percent calcium halide, the halide being 0.3-0.6 percent bromide and about 99.4-99.7 percent chloride. Both compositions of salts of U.S. Pat. No. 7,541,052 and WOo 1/00218 differ largely from the composition of human plasma and human airway (nose) surface fluids. According to Joris et al, the composition of airway surface fluid and plasma levels in human volunteers is Na (mM) 82 and 139, K (mM) 29 and 4, and Ca (mM) 4 and 2.4 (Joris et al, Elemental composition of human airway surface fluid in healthy and diseases airways, Am. Rev. Respir. Dis. 1993; 148:1633-1637). The extremely large amounts of magnesium salts, the presence of bromides, and the overall composition of U.S. Pat. No. 7,541,052 and WOoi/00218 differ completely from the present disclosure composition. The composition of the present disclosure composition contains sodium, potassium and calcium salts (as chloride) in physiologically acceptable amounts, and in a concentration largely comparable to the concentration present in human plasma and human airway surface fluid.

The applicants have surprisingly found that nasal compositions containing low-concentrations of caffeine and/or theobromine advantageously work as a ciliary stimulant when administered in an aqueous composition at a pH of about 6-8, containing also—sodium, calcium and potassium salts, preferably selected from NaCl, KCl, CaCL, and optionally also containing $NaHCO_3$, glucose, various buffers and/or small amounts of other inorganic salts and/or other salts such as acetates, lactates, sulphates and phosphates. By using these low concentrations of caffeine any potential central stimulating effect of caffeine is avoided, because the total amount of caffeine administered is negligible and serves only to stimulate ciliary activity in the nose. Also, solubility problems with caffeine in aqueous compositions (requiring the use of solubilizers and/or complex formation by sodium benzoate) are avoided when such low concentrations of caffeine are used.

SUMMARY OF THE PRESENT DISCLOSURE

In one aspect, the present disclosure provides an aqueous nasal composition comprising caffeine and/or theobromine in a total concentration of up to about 0.5 percent (w/v) and an aqueous carrier having a pH of 6-8 and comprising physiologically acceptable potassium, calcium and sodium salts. Caffeine and/or theobromine increase ciliary beat frequency and stimulate ciliary activity, whilst the salts in the composition at the same time surprisingly support and enhance this effect.

Preferably, the compositions of the present disclosure may further comprise chloride ions; hence, the sodium, potassium and/or calcium salts in the composition may suitably be provided in the form of NaCl, KCl and/or CaCL respectively. Suitably, the composition may comprise about 80-200 mM $Na^+$, about 1-10 mM $K^-$ and/or about 0.5-7 mM $Ca^{2+}$ ions.

This composition may be used for the treatment of nasal congestion or common cold, for nasal cleansing or for the prevention of nasal allergic and infectious diseases. More generally, the composition of the present disclosure may be used for increasing nasal ciliary beat frequency and/or stimulating nasal mucociliary clearance.

In another aspect, the present disclosure provides a method for treating nasal congestion or common cold, for nasal cleansing or the prevention of nasal allergic and infectious diseases, which comprises administering the composition of the present disclosure to the nose of a patient.

This composition may be provided in the form of a nasal spray or nasal drops or nasal irrigation fluid or wash, in a specific composition able to stimulate nasal ciliary movement and mucociliary clearance and to decrease the nasal mucus transit time (MIT). The composition of the present disclosure is also able to clean the nasal passages and to remove noxious materials as soon as possible to prevent viral, bacterial and allergic diseases in the upper airways and can be used for a longer period of time than the current decongestants.

The applicants have found that the combination of a salt solution containing sodium, calcium and potassium salts with a small amount of caffeine and/or theobromine produces a surprising enhancement in ciliary movement, thereby improving mucociliary clearance. In particular, it has been found during experiments with human nasal cells, that caffeine in a very low concentration (up to about 5 mg/ml) in an isotonic aqueous solution, containing also sodium, potassium and calcium salts and optionally also $NaHCO_3$ and glucose, increases the ciliary beat frequency by an activation of the ciliary movement measured by a strong increase in ciliary beat frequency. The major part of the caffeine or theobromine administered will be absorbed after swallowing in the gastrointestinal tract into the blood, but this amount is extremely low in comparison with the amounts of caffeine absorbed in humans of all ages in daily life.

Advantageously, the aqueous carrier of the present disclosure may be isotonic to normal bodily fluids, in order to bring about optimal improvement in mucociliary clearance. However, hypotonic or hypertonic formulations may also be used. In a particularly preferred embodiment, the aqueous carrier is an enriched saline solution, such as Ringer's solution, Locke-Ringer solution, Lactated or Ace to ted Ringer's solution, Krebs solution, Krebs-Ringer solution, Tyrode or Hartman's solution, or other similar solutions. The composition and formulation of such solutions is well known in the art.

Also, the present disclosure composition provides a nasal formulation for use in the treatment of nasal congestion, the common cold and in the prevention of nasal infectious and allergic diseases, wherein the nasal composition is administered in a dosage regimen, wherein the nasal medication can be administered, as needed, daily, for example every 2-6 hours, and/or for a period, if needed, longer than 3 days or 3-5 days, or longer than 5 days, or longer than a week, or longer than 2 weeks, or longer than a month, or over an unlimited or unspecified period of time. Further, an object of the present disclosure is to provide a method for manufacturing such a nasal formulation. A further object of the present disclosure is to provide a method of spraying or otherwise administering a solution into a nostril, to clean the nasal passages, and to stimulate ciliary function.

DETAILED DESCRIPTION OF THE PRESENT DISCLOSURE

Caffeine as described in the present disclosure is intended to cover all caffeine forms described in the pharmaceutical literature, such as caffeine, caffeine hydrate, caffeine citrate and other pharmaceutical acceptable forms. Caffeine is naturally produced by several plants, including coffee beans, guarana, cacao beans, and tea. Caffeine stimulates the central nervous system, heart rate, and respiration, has psychotropic (mood altering) properties, and acts as a mild diuretic. A normal dose of caffeine is generally considered to be 100 mg, which is roughly the amount found in a cup of coffee. Caffeine is generally consumed in coffee, cola, chocolate, and tea, although it is also available as a stimulant. Caffeine (=1,3,7-trimethylxanthine) belongs to a group of alkaloids called methylxanthines. Also theobromine (3,7 dimethylxanthine) and theophylline (1,3 dimethylxanthine) belong to this group. They have similar pharmacological properties, occur together with caffeine, but in much smaller amounts, in natural products and they are both formed in the human body as minor metabolites (through demethylation) of caffeine.

Caffeine and/or theobromine in the present disclosure is used in an aqueous solution in a low concentration, up to about 5 mg/ml, which is equivalent to 0.5 percent (w/v). The compositions of the present disclosure may, for example, comprise about 0.001 percent-0.5 percent (w/v) caffeine and/or theobromine. The compositions of the present disclosure may comprise less than 0.5 percent (w/v) caffeine and/or theobromine. Furthermore, in some embodiments, the compositions of the present disclosure may comprise up to about 0.45 percent (w/v) caffeine and/or theobromine, or up to about 0.4 percent (w/v), or up to about 0.3 percent (w/v), or up to about 0.25 percent (w/v), or up to about 0.2 percent (w/v), more preferably about 0.2 percent (w/v) or about 0.1 percent (w/v), or about 0.01 percent (w/v), or as little as about 0.005 percent (w/v) or about 0.001 percent (w/v). It works perfectly in this low concentration as a ciliary stimulant. No higher concentrations are needed. The amount of caffeine of for instance about 2 mg/ml (0.2 percent w/v) is very modest. Systemic absorption of this small amount of caffeine even when using several ml of this formulation per day is negligible in comparison with the daily intake of caffeine. Further, in young children it is possible to adapt the volume of the present disclosure to small volumes of for instance about 25 or 50 or 70 or 90 µl containing about 0.2 percent caffeine/theobromine. In other embodiments the concentration of caffeine and/or theobromine can be less than about 0.2 percent, or less than about 0.1 percent and or less than about 0.01 percent (w/v).

In particular, when the volume administered is larger than for instance 100 µl and/or if the volume per nostril used is much larger, it is advisable to use the present disclosure composition in which the caffeine concentration is less than about 0.2 percent, less than about 0.1 percent, less than about 0.05 percent or less than about 0.01 percent (w/v). Suitably, the concentration of caffeine and/or theobromine in the compositions of the present disclosure may be at least 0.001 percent (w/v). In some preferred embodiments, the concentration of caffeine and/or theobromine is in the range 0.001 percent (w/v) to less than 0.5 percent (w/v). The concentration of caffeine and/or theobromine in the compositions of the present disclosure may be at least about 0.005 percent (w/v). In some embodiments, the concentration of caffeine and/or theobromine may be at least about 0.01 percent, or at least about 0.02 percent, or at least about 0.03 percent, or at least about 0.04 percent, or at least about 0.05 percent, or at least about 0.06 percent, or at least about 0.07 percent, or at least about 0.08 percent, or at least about 0.09 percent, or at least about 0.1 percent (w/v).

It will be understood that when both caffeine and theobromine are used in a composition according to the present disclosure, the "total concentration" refers to the overall concentration of both of these methylxanthines in the composition.

In the present disclosure composition caffeine and/or theobromine contributes strongly to the stimulating effects on the ciliary movement and mucociliary clearance, providing a nasal formulation for use in the treatment of nasal congestion, common cold, for nasal cleaning and prevention of nasal infectious and allergic diseases. Also the present disclosure provides a new dosage regimen, wherein the nasal medication can be administered, as needed, daily about every 2-6 hours, and for a period, if needed, longer than about 5 days. This is in sharp contrast with the widely used decongestants. Their use is restricted to about 3-5 days because decongestants are associated with a rebound phenomenon, Rhinitis medicamentosa, causing a long-lasting rhinosinusitis. However, the compositions of the present disclosure may be used and administered for much longer periods of time, even over an unlimited period of time, without detriment to the patient.

Thus, the present disclosure provides a composition as hereinbefore and hereinafter described, for administration to a patient over a period of longer than 3-5 days, or longer than 5 days, or longer than a week, or over an unlimited or unspecified period of time, and/or for daily or regular administration, such as every 2-6 hours, or about every 4 hours, or once, twice or more each day.

When the present disclosure composition is administered very frequently during the day and the total volume administered is larger than for instance about 3 ml, or 4 ml or 5 ml, it is advisable to use a composition in which the caffeine concentration is less than about 0.2 percent, less than about 0.1 percent, less than about 0.05 percent or between about 0.05 and 0.01 percent (w/v).

Administered as nasal medication in for instance a volume of 100 µl the administered dose of caffeine may be about 0.010 mg, 0.10 mg, 0.2 mg or 0.5 mg. This means that only a very small amount of caffeine is required to activate the ciliary movement in the nasal cavity. The major part of caffeine will be absorbed after swallowing in the gastrointestinal tract into the blood. This amount is extremely low in comparison with the amounts of caffeine absorbed in humans of all ages after a cup of coffee (50-100 mg caffeine), a Upton cup of black tea and green tea (55 and 45 mg of caffeine) or a coca cola classic (35 mg caffeine) or an energy drink (Red Bull 76-80 mg caffeine). The amount of theobromine in coffees and teas is in relative terms only about 10 percent of the amount of caffeine and the amount of theophylline is even much less. Total amounts of caffeine consumed in the Western world per individual can be found in the literature and are about 300 mg per day. In the adult population, a moderate daily caffeine intake at a dose level <400 mg per day, which is equivalent to about 6 mg/kg bodyweight, is not associated with adverse effects (Nawrot et al., Food Additives Contaminants 2003; 1:1-30).

This means that the dose of caffeine administered when using the nasal composition of the present disclosure is extremely low.

A composition of the present disclosure comprises $Na^+$, $K^+$ and $Ca^{2+}$ ions in a formulation which may preferably be substantially isotonic to normal bodily fluids, but may alternatively be hypotonic or hypertonic. In particular, the concentration of salts and ions in a composition according to the present disclosure may be up to about 50 percent higher or up to about 50 percent lower than isotonic. Optionally, the concentration of salts and ions may be up to about 40 percent higher, or up to about 30 percent higher, or up to about 20 percent higher, or up to about 10 percent higher than isotonic. Alternatively, the concentration of salts and ions may be up to about 40 percent lower, or up to about 30 percent lower, or up to about 20 percent lower, or up to about 10 percent lower than isotonic.

In a preferred embodiment, the aqueous carrier of the present disclosure is an enriched saline solution or a mixture of these solutions, well known in the art and described in many places in the literature. Examples are Ringer solution, Locke-Ringer solution, Lactated or Acetated Ringer, Krebs solution, Krebs-Ringer solution, Tyrode, or Hartman's solution, and others, all comprising balanced quantities of sodium, potassium and calcium salts (mainly chlorides) in various concentrations. Examples of these concentrations for respectively a, K, and Ca, expressed in raM, are: Ringer: 147, 4.2, and 2.25; Locke Ringer: 154, 5.6, and 1.1; Krebs solution: 118, 4.7, and 2.5; Krebs-Ringer solution: 115, 5.9, and 2.5; Tyrode solution: 138, 2.7, and 1.8; Hartman's solution: 131; 5, and 2. These solutions may also contain glucose, sodium bicarbonate, various buffers, and occasionally small amounts of magnesium salts and other salts like acetates, lactates, sulphates and phosphates.

The compositions of the present disclosure comprise physiologically acceptable salts of sodium, potassium and calcium. Suitably, the compositions of the present disclosure may comprise at least about 80 mM, preferably at least about 100 mM, or at least about 110 mM, or at least about 120 mM or at least about 150 mM $Na^+$. The compositions of the present disclosure may comprise up to about 200 mM, or up to about 180 mM, or up to about 160 mM or up to about 150 mM $Na^+$. Optionally, the compositions may comprise about 130-145 mM $Na^+$. In some preferred embodiments, the $Na^+$ ions are provided in the form of NaCl. 0.0585 mg/ml (or 0.00585 percent w/v) NaCl is equivalent to 1 mM $Na^+$. The compositions of the present disclosure may optionally comprise about 0.62-0.93 percent (w/v) NaCl which is equivalent to about 106-159 mM $Na^+$. Suitably, the compositions of the present disclosure may comprise NaCl at a concentration which is isotonic or within about 10 percent of isotonic to normal bodily fluids.

Suitably, the compositions of the present disclosure may comprise at least about 1 mM, preferably at least about 2.5 mM, or at least about 3 mM, or at least about 5 mM or at least about 6 mM $K^+$. The compositions of the present disclosure may comprise up to about 10 mM or up to about 7 mM or up to about 6.5 mM K. In some preferred embodiments, the $K^+$ ions are provided in the form of KCl. 0.0745 mg/ml (or 0.00745 percent w/v) KCl is equivalent to 1 mM $K^+$. The compositions of the present disclosure may optionally comprise about 0.034-0.050 percent (w/v) KCl which is equivalent to about 5-7 mM $K^+$. Suitably, the compositions of the present disclosure may comprise KCl at a concentration which is isotonic or within about 10 percent of isotonic to normal bodily fluids.

Suitably, the compositions of the present disclosure may comprise at least about 0.5 mM, preferably at least about 1 mM, or at least about 3 mM or at least about 5 mM $Ca^{2+}$. The compositions of the present disclosure may comprise up to about 7 mM, or up to about 6 mM, or up to about 5 mM or up to about 4 mM $Ca^{2+}$. Optionally, the compositions may comprise between about 1-2.5 mM $Ca^{2+}$. In some preferred embodiments, the $Ca^{2+}$ ions are provided in the form of $CaCl_2$, preferably $CaCl_2.2H_2O$. 0.147 mg/ml (or 0.0147 percent w/v) $CaCl.2H_2O$ is equivalent to 1 mM $Ca^{2+}$. The compositions of the present disclosure may optionally comprise about 0.013-0.019 percent (w/v) $CaCl_2.2H_2O$ which is equivalent to about 0.9-1.3 mM $Ca^{2+}$. Suitably, the compositions of the present disclosure may comprise $CaCl_2$ at a concentration which is isotonic or within about 10 percent of isotonic to normal bodily fluids.

The composition of the present present disclosure may advantageously comprise a buffering agent such as $NaHCO_3$. The buffering agent may be provided at a concentration capable of maintaining the pH of the composition at about 6-8, preferably about 7-7.5, or about 7.3-7.5, more preferably about 7.4. Thus, the composition may comprise at least about 0.01 percent (w/v) $NaHCO_3$ or at least about 0.012 percent (w/v) $NaHCO_3$. The composition may comprise up to about 0.1 percent (w/v) $NaHCO_3$, or up to about 0.02 percent (w/v) $NaHCO_3$, or up to about 0.018 percent (w/v) $NaHCO_3$. In one optional embodiment, the composition comprises about 0.012-0.018 percent (w/v) $NaHCO_3$.

The composition of the present disclosure may advantageously comprise a saccharide such as glucose; for example, at least about 0.05 percent (w/v) glucose, or at least about 0.08 percent (w/v) glucose or at least about 0.1 percent (w/v) glucose. The composition may comprise up to about 2 percent (w/v) glucose or up to about 1 percent (w/v) glucose or up to about 0.2 percent (w/v) glucose or up to about 0.15 percent (w/v) glucose or up to about 0.12 percent (w/v) glucose. In one optional embodiment, the composition comprises about 0.08-0.12 percent (w/v) glucose.

A particularly preferred embodiment of the present disclosure compositions meets the object of stimulating the nasal mucociliary clearance by including into the formulation a solution containing about 0.772 percent (w/v) NaCl, 0.042 percent (w/v) KCl, 0.016 percent (w/v) $CaCl_2.2H_2O$, 0.015 percent (w/v) $NaHCO_3$ and 0.1 percent (w/v) glucose. This solution stimulates ciliary activity, because in "in vitro" experiments we have found that, even after 1-2 hours the ciliary beat frequency (CBF) of ciliated tissue in this solution is still unaffected and sometimes even higher, while under similar conditions in experiments with saline (=0.9 percent NaCl, w/v) a reduction in CBF of about 30 percent was found.

In many publications it has been proven that preservatives (like thiomersal, benzalkoniumchloride and others), widely used in nasal medications, severely disturb the ciliary activity. It is therefore a further benefit of the present disclosure that the use of any preservative can be avoided by providing a sterile nasal solution and a sterile nasal container for the application of the present disclosure composition into the nose. Preferably, therefore, the compositions of the present disclosure may be free from preservatives, for example thiomersal, benzalkoniumchloride, benzoic acid, sodium benzoate or others. The compositions of the present disclosure are preferably also free from decongestants. As a consequence the compositions of the present disclosure do not cause any "rebound congestion" and hence may be usable without adverse effects frequently and over a period of time longer than about 3-5 days, and may be usable over an unlimited period of time.

The present disclosure compositions provides sterile aqueous nasal compositions for spraying or dropping into a nostril or as nasal irrigation fluid, comprising more than 90 percent (v/v) water, a ciliary stimulant, for instance caffeine and inorganic salts in a specific compositions and pH, and optionally sugar alcohols, such as mannitol, sorbitol, xylitol, saccharides such as glucose, viscosity modulators such as HPMC and flavoring agents, such as menthol, camphor, and eucalyptol. Preferably the composition may be isotonic, but also hypotonic and hypertonic solutions may be used, and the pH should be between about 6-8, preferably between about 7-7.5, more preferably about pH 7.4.

Other preferred embodiments of the present disclosure compositions provide a sterile aqueous nasal composition comprising 0.001-0.5 percent (w/v) or 0.1-0.5 percent (w/v) of caffeine and/or theobromine, and an aqueous carrier with a pH between 6-8, comprising 0.62-0.93 percent (w/v) NaCl, 0.034-0.050 percent (w/v) KCl, 0.013-0.019 percent (w/v) $CaCl_2.H_2O$, 0.012-0.018 percent (w/) $NaHCO_3$ and 0.08-0.12 percent (w/v) glucose. Optionally, said composition may be diluted with water; in particular, the above-mentioned composition may optionally comprise 5-40 percent (v/v) of water and 60-95 percent of said aqueous carrier. By spraying or dropping about 25-150 µl, such as 25-50-75-100-125-150 µl, of such compositions into the nose, by single or multiple administration, the nasal passages will be cleaned, the ciliary movement activated and the nasal mucociliary clearance will be stimulated causing a decrease of 5-50 percent of the MTT, resulting in a fast removal of viruses, bacteria and other noxious material in order to treat and prevent viral, bacterial, and allergic diseases in the upper airways. Also much larger volumes up to about 250-2000 µl, such as 250-500-1000-2000 µl, or even much larger volumes can be used for nasal and sinus irrigation, but in those cases the concentration of the methylxanthine may have to be reduced to levels between 0.001-0.1 percent or between 0.01-0.05 percent (w/v). Such compositions are suitable for use in the treatment of nasal congestion and in the prevention of nasal allergic and infectious diseases, wherein the nasal composition may be administered, as needed, daily, for example about every 4 hours or every 2-6 hours, and for a period longer than 3 or longer than 5 days.

This new dosage regimen is a large improvement over the current dosage regimen of decongestants. For instance the dosage regimen recommended by the FDA for the use of a decongestant like xylometazoline (Otrivin) is: Do not use xylometazoline nasal for longer than 3 to 5 days. Longer use could cause damage to the nasal tissue and lead to chronic congestion. Do not use xylometazoline in larger doses or more often than is recommended. Too much xylometazoline nasal could be harmful. Xylometazoline nasal should not be used more often than two to three times a day, every 8 to 10 hours (source 2012: emedicinehealth.com).

In case the user of the nasal spray according to the present disclosure does not want to use a methylxanthine as ingredient in the composition or when a methylxanthine is not indicated to be included in the composition for medical or commercial reasons, the methylxanthine in the composition can be reduced to about 0.001 percent-0.01 percent (w/v) or supplemented with about 0.01-2 percent (w/v) mannitol or sorbitol or another suitable sugar alcohol or by about 0.01-2 percent (w/v) glucose or another suitable saccharide. In a further embodiment the methylxanthine in the formulations can be replaced partly by ascorbic acid, or ascorbic acid can be used as an additional ingredient, because we have found in several "in vitro" experiments with ciliated cells, that ascorbic acid increases the ciliary beat frequency and consequently may be expected to improve the mucociliary clearance "in vivo". When ascorbic acid is added to the present disclosure composition, the pH of the final composition should be adapted to values between about 6-8 and preferably between about pH 7-7.5 by adding a small amount of sodium bicarbonate or other pH regulating agents.

In other embodiments the present disclosure compositions comprise other excipients such as inorganic salts, mannitol, sorbitol, xylitol, saccharides such as glucose, viscosity modulators such as HPMC and flavouring agents such as menthol, camphor or eucalyptol. In particular, the compositions of the present disclosure may comprise ascorbic acid at about 0.1-1 percent (w/v) mannitol at about 0.01-5 percent (w/v), sorbitol at about 0.01-5 percent (w/v), xylitol at about 0.01-5 percent (w/v), menthol at about 0-0.75 percent (w/v), eucalyptol at about 0-0.15 percent (w/v), camphor at about 0-0.15 percent (w/v), HPMC at about 0-4 percent (w/v) and as flavoring agent: Spearmint Flavor IFF SN 785643 q.s. These excipients are only examples and can be replaced by similar excipients known from the pharmaceutical literature as excipients used in nasal liquid medications.

In some preferred embodiments of the present disclosure, the caffeine and/or theobromine are provided in the form of a natural ingredient. The nasal compositions of the present disclosure may contain caffeine and another methylxanthine (theobromine, theophylline) or a combination of these compounds in the form as they occur in many plants, such as coffee (e.g. Coffea arabica and Coffea robust a), tea (e.g. Camellia sinensis), cocoa (Theobroma cacao), Yerba mate plant and Cola plant, and/or in the form as they occur in products from these plants. For instance in the form as they are used in daily life in coffee, tea, cola or chocolate products. Infusions, including aqueous infusions, extracts, teas and other galenical preparations from these plants, containing caffeine, and/or theobromine, and/or theophylline can selected to be included in the present disclosure compositions. For instance, the nasal composition of the present disclosure may contain in some embodiments about 1 percent-50 percent (v/v) or about 50 percent-99 percent (v/v) of an aqueous infusion, extract, tea or another (liquid, semi-liquid, solid, dry or freeze-dried) galenical preparation from one or more plant products, containing caffeine and optionally small amounts of theobromine, and theophylline.

The exact amount of the methylxanthine in the final nasal composition may be measured and may be in the range of about 0.001 percent-0.5 (w/v). As an example, methylxanthine contents in different brews of tea differ substantially dependent on the type of tea used: black, oolong, green and herbal. By measuring the caffeine and/or theobromine and/or theophylline content, it is possible to add the required amount of tea brew to the nasal composition to bring the final caffeine and/or other methylxanthine content to for instance about 0.1 or 0.5 percent or any other requested concentration in the range of 0.001 percent-0.5 percent (w/v), being the total content of the methylxanthines. In this respect it is good to realize, that in teas the content of theobromine is generally about 10 percent of the content of caffeine. If a tea brew or extract is used as a ingredient in the present disclosure compositions, it has to be taken into account that, for instance, about 90 percent of the total amount of methylxan thines consists of caffeine and about 10 percent of theobromine. When such a tea brew or extract is used as a part of the total nasal composition of the present disclosure, the infusion, brew or extract or tea can be diluted, if needed, with sterile water to obtain the required content of caffeine and/or theobromine. Or both methylxanthines, caffeine and theobromine, preferably in a concentration ratio of caffeiner:theobromine of 90 percent:io percent, can be added during the manufacturing of the nasal composition of the present disclosure in order to obtain the required total concentration of the individual methylxanthine. Manufacturing is completed by adding the ingredients NaCl, KCl, $CaCl_2.2H_2O$, and optionally $NaHCO_3$ and glucose in an amount to obtain a concentration in the final nasal composition in the range of: about 0.62-0.93 percent (w/v) NaCl, 0.034-0.050 percent (w/v) KCl, 0.013-0.019 percent (w/v)

$CaCl_2.2H_2O$, 0.012-0.018 percent (w/v) $NaHCO_3$ and 0.08-0.12 percent (w/v) glucose. Optionally also ascorbic acid and/or mannitol as ciliary stimulants can be included in the nasal composition of the present disclosure in concentrations between about 0.1-1 percent (w/v) or between about 0.01 and 1 percent (w/v).

The dispenser or device comprising the present disclosure composition may be a conventional bottle used for nasal drops. In preferred embodiments the composition is presented as a device using a metered pump spray for nasal delivery or pressurized aerosols (Bag-on-Valves and Dip tubes) or Mono dose devices or Squeeze or electric powered devices.

A preferred multidose nasal spray apparatus is the Bag-on-Valves device. Another is the so-called APF pump, fitted with a glass or plastic bottle as reservoir, delivering a accurate spray volume of for instance 50-150 µl, such as 50-70-90-100-125-150 µl. The spray characteristics show that only a very small percentage of the droplets is smaller than about 10-20 µm in diameter and 90 percent are smaller than 300 µm in diameter. For instance, the present disclosure compositions can be administered as a sterile aqueous nasal composition in a nasal spray consisting of a container and a spray pump delivering about 25-150 µl, such as 25-50-70-75-90-100-125-150 µl, per activation. Also, sterile aqueous nasal composition in unit-dose devices for nasal administration, for single or multiple administration, as a single drop or as multiple drops, in a total volume of about 25-150 µl, such as 25-50-70-75-90-100-125-150 µl, per administration are suitable to administer the present disclosure composition into the nose of a human subject.

The present disclosure also provides a method of manufacturing a sterile aqueous composition for use in stimulating the ciliary activity and mucociliary clearance of the nose. The method comprises obtaining in a container a quantity of water that is more than 90 percent of total volume, adding of one or more ciliary stimulants, for instance caffeine, or caffeine and theobromine, or adding the required amount of methylxanthine in the required volume of the plant extract or infusion, and/or ascorbic acid. The next step consists of adding specific quantities of inorganic salts, adjusting the pH between pH 6-8, preferably between 7-7.5, more preferably between 7.3-7.5, optionally adding viscosity modulators, sugar alcohols, saccharides, flavoring agents and/or other GRAS excipients known from the pharmaceutical literature to be included in nasal formulations. Next steps are stirring the composition to ensure dissolution of all components in the water carrier, adjusting the final batch volume with water, sterilizing the total composition by filtration, gamma sterilisation or elevated temperature (100 or 120 degrees Celsius) and packaging the composition in a suitable device for nasal administration.

Based on the foregoing present disclosure of new nasal compositions, it should be apparent that the teachings of the present disclosure can be implemented in a variety of forms. Therefore certain variations in the ingredients of the present disclosure compositions can be implemented by those skilled in the art. Especially the inclusion or omitting an ingredient and the variation in the concentration of the ingredients such as NaCl, KCl, $CaCl_2$, $NaHCO_3$, and glucose, and/or a possible inclusion of further ingredients such as inorganic salts other than described in the specification of this application, other buffers, flavouring agents, vitamins, pH regulators, sugar alcohols, other saccharides etc. will fall within the scope of the claimed present disclosure.

Experimental Section (1)

Ciliary beat frequency (CBF) measurements were performed on the ciliated epithelium of isolated chicken embryo trachea. The chicken embryo trachea was dissected from the embryo and sliced into small rings of approximately 0.5 mm to 1 mm thickness. The trachea slices were placed in stainless steel supporting rings. They were allowed to recover for 30 minutes in a solution, containing per liter of Millipore-deionized water: NaCl, 7.72 g (132 mmol); KCl, 0.42 g (5.63 mmol); CaCl2.21120, 0.16 g (1.09 mmol); $NaHCO_3$, 0.15 g (1.79 mmol); glucose, 1.00 g (5.55 mmol). This solution was sterilized for 20 minutes at 120 degrees centigrade and after cooling the pH of the solution was established at 7.4. CBF was measured by using an Olympus BH-2 light microscope. The microscope table was connected with a thermostat to maintain a temperature of 33 degrees centigrade The CBF was subsequently monitored using a photo-electric registration device. Procedure: A light beam was transmitted through the moving cilia, and after magnification by the microscope the flickering light was projected to a photocell. The electrical signal generated by this photocell was visualized with a computer monitor. The frequency of the signal was calculated electronically by Fast-Fourier transform algorithm and displayed as a frequency distribution.

All CBF data were calculated as the relative frequency of the initial frequency at the start of the experiments, the latter being expressed as 100 percent. After measuring of the initial CBF, the ciliated tissue samples were put in a well containing 1.0 mL of the test solution 15 percent propylene glycol (v/v) in water and the CBF was measured after 5 minutes. The CBF appeared to be strongly reduced after 5 minutes to about only 40 percent of the original CBF.

In order to test the reversibility of the impaired CBF, the ciliated tissue samples were washed by shaking them vigorously in a tube with 3 mL of a test solution called "Saline solution" (0.9 percent w/v NaCl) and the CBF was measured again every 5 to 10 minutes until 60 minutes after the start of the incubation. Tissue samples of 5 different chickens were tested and the resulting recovery of the CBF was measured.

Similar experiments were carried out with a composition called Ciliactive® (containing NaCl 7.41 g and enriched by Caffeine 2.00 g, KCl 0.403 g, $CaCl_2$ 1.16 g, $NaHCO_3$ 0.144 g glucose 0.96 g, dissolved in 1 liter of Millipore-deionized water, with a pH of 7.4 and sterilized 20 min. at 100 degrees Celsius).

The results summarized in FIG. 1 demonstrate that pre-treatment with 15 percent (v/v) propylene glycol in water has a detrimental influence on the CBF. Already after 5 minutes the CBF has been reduced to about 40 percent of the original CBF. Subsequent rinsing with Saline solution did not restore the CBF in the following 55 minutes. This is in sharp contrast with the recovery of the CBF within about 10-15 minutes after rinsing with Ciliactive®. From FIG. 1 it is clear that the Ciliactive® composition has a strong stimulating effect on the ciliary movement. Ciliactive® causes a complete recovery of the CBF (expressed as white bars), while the Saline solution (expressed as black bars) is not able to stimulate the ciliary beat frequency.

The experiments show that the aqueous nasal composition called Ciliactive®, comprising a very low concentration of caffeine in a specific and carefully balanced combination with the other ingredients NaCl, KCl, $CaCl_2$, $NaHCO_3$ and glucose, is able to strongly stimulate impaired ciliary activity.

Experimental Section (2)

Influence of Ciliactive® on the ciliary beat frequency (CBF) of human nasal ciliated epithelial cells was measured in monolayer cell cultures of human nasal cells. These nasal cells expressing beating cilia were obtained from surgery specimens. After isolation of nasal epithelial cells they were evaluated for normal, coordinated ciliary activity and seeded in culture flasks coated with a collagen gel. The cell density was high enough (50000 cells/cm$^2$) that after 3-5 days the cell cultures were confluent and contain differentiated ciliated epithelium, suitable to measure the CBF. CBF was measured on 11 different places in the nasal cell cultures using an inverted microscope coupled with a high-speed digital camera. The CBF was analyzed with Matlab software which slows down the movies of the ciliary beating and interprets the beat frequency.

Part 1.

Ciliated cells were exposed to culture medium and to culture medium containing 50 percent Ciliactive® (v/v) for 24 hours. CBF was measured after 24 hours. Results: CBF (in Hertz) as measured (n=11) after 24 hours exposure to:

| Culture medium | culture medium-Ciliactive ® 50 percent: 50 percent v/v) |
|---|---|
| 10.55 | 14.20 |
| 11.89 | 12.68 |
| 8.19 | 9.81 |
| 7.99 | 12.78 |
| 9.14 | 11.65 |
| 11.15 | 14.46 |
| 9.50 | 13.62 |
| 10.15 | 14.85 |
| 9.59 | 9.84 |
| 8.79 | 10.74 |
| 6.88 | 11.22 |
| mean 9.44 | mean 12.35 |
| (sd 1.46) | (sd 1.82) |

Results:

Human nasal epithelial cells in contact with Ciliactive® show a significant increase of CBF after 24 hours. The mean increase in CBF was from 9.44 Hertz to 12.35 Hertz, which an increase of about 31 percent. The unpaired t-test of these results shows that the increase of CBF after exposure to culture medium enriched with Ciliactive®, compared to culture medium alone, is extremely statistically significant (two tailed p-value equals 0.0005).

Part 2.

A similar experiment (as presented in part 1) has been carried out with culture medium and culture medium, containing 50 percent (v/v) NaCl (0.9 percent w/v, also called Saline). After 24 hours there was no significant increase or decrease of the CBF values, indicating that saline has no stimulating effect on the ciliary activity.

Part 3.

Human nasal ciliated cells were exposed to culture medium containing 75 percent Saline (=0.9 percent NaCl w/v) and to culture medium containing 75 percent Ciliactive® (v/v). CBF was measured at t=o and t=5 hours, 24 hours and 48 hours and the difference between the two sets of results was measured.

A pool of cell cultures of human nasal epithelial cells was randomly sorted into two separate (independent) groups. The two groups were treated differently with respect to an independent variable (75 percent Ciliactive-25 percent culture medium) or (75 percent Saline-25 percent culture medium). Next step was measuring in all culture samples of both groups the change in CBF after 5 hours, 24 hours and 48 hours with the aim of determining whether the treatment with either Ciliactive® or Saline produces differential effects.

At t=o the CBF level in every cell culture sample of both separate groups was measured and that level was set at 100 percent. The change in CBF after 5 hours was expressed in a percentage in relation the start level. For example, a CBF of 140 percent after 5 hours is indicating that the CBF has increased 40 percent and 85 percent means that the CBF levels has decreased by 15 percent. Also a randomly chosen separate group of cell cultures was treated only with culture medium. As a control the CBF was measured in a similar way, also at t=o and t=5, 24, and 48 hours.

Results:

A. Mean increase in CBF after 5 hours (expressed as percentage and related to 100 percent at t=o) as measured in nasal epithelial ciliated cells exposed to culture medium (CM), to CM-75 percent Saline and to CM-75 percent Ciliactive®:

| CM (control value) | CM-75 percent Saline | CM-75 percent percent Ciliactive ® |
|---|---|---|
| 123.49 percent | 126.23 percent | 153.25 percent |
| SD 35 percent | SD 22 percent | SD 32 percent |
| N = 18 | N = 21 | N = 23 |

The results demonstrate a substantial increase of CBF, up to 153.25 percent, after 5 hours due to Ciliactive®. The unpaired t-test indicates that this increase of the CBF in the human nasal cells exposed to culture medium enriched with 75 percent (v/v) Ciliactive®, compared to the samples containing 75 percent (v/v) Saline, is very statistically significant (two tailed p-value equals 0.003)

B. Mean increase in CBF after 24 hours (expressed as percentage and related to 100 percent at t=o) as measured in nasal epithelial ciliated cells exposed to culture medium (CM), to CM-75 percent NaCl (0.9 percent) and to CM-75 percent Ciliactive®:

| CM (control value) | CM-75 percent Saline | CM-75 percent percent Ciliactive ® |
|---|---|---|
| 105.80 percent | 108.36 percent | 134.84 percent |
| SD 22 percent | SD 17 percent | SD 27 percent |
| N = 18 | N = 18 | N = 20 |

The results demonstrate a substantial increase of CBF after 24 hours due to Ciliactive®. The unpaired t-test indicates that this increase of the CBF in the human nasal cells exposed to culture medium enriched with 75 percent (v/v) Ciliactive®, compared to the samples containing 75 percent (v/v) Saline, is very statistically significant (two tailed p-value equals 0.001)

C. Mean increase in CBF after 48 hours (expressed as percentage and related to 100 percent at t=o) as measured in nasal epithelial ciliated cells exposed to culture medium (CM), to CM-75 percent NaCl (0.9 percent) and to CM-75 percent Ciliactive®:

| CM (control value) | CM-75 percent Saline | CM-75 percent percent Ciliactive ® |
|---|---|---|
| 98.15 percent | 101.58 percent | 124.19 percent |
| SD 15 percent | SD 14 percent | SD 24 percent |
| N = 11 | N = 15 | N = 14 |

The results demonstrate a substantial increase of CBF after 48 hours due to Ciliactive®. The unpaired t-test indicates that this increase of the CBF in the human nasal cells exposed to culture medium enriched with 75 percent (v/v) Ciliactive®, compared to the samples containing 75 percent (v/v) Saline, is very statistically significant (two tailed p-value equals 0.005)

Conclusion: The experiments demonstrate, that Ciliactive® increases ciliary activity in human nasal cells with about 20-30 percent as measured by the increase in Ciliary Beat Frequency. Compared with the effect of Saline (NaCl 0.9 percent w/v), the increase under the influence of Ciliactive® is very statistically significant after 5, 24, and 48 hours.

What is claimed is:

1. A method for the treatment of a human subject in need of nasal cleansing, or suffering from nasal congestion or common cold, or for the prevention of nasal infectious diseases or nasal allergic diseases, the method comprising:
    administering to the nose of the human subject an aqueous nasal composition comprising:
        a total concentration of caffeine from 0.001% (w/v) to 0.3% (w/v);
        an aqueous carrier having a pH from about 6 to about 8, the aqueous carrier comprising sodium ions from a physiologically acceptable sodium salt, potassium ions from a physiologically acceptable potassium salt, and calcium ions from a physiologically acceptable calcium salt,
        wherein the aqueous nasal composition is isotonic, hypertonic, or hypotonic to normal fluids of human nasal passages, and wherein in the aqueous nasal composition:
            the physiologically acceptable sodium salt is sodium chloride (NaCl);
            the physiologically acceptable potassium salt is potassium chloride (KCl); and
            the physiologically acceptable calcium salt is calcium chloride ($CaCl_2.2H_2O$).

2. The method of claim 1, wherein the aqueous nasal composition comprises an aqueous infusion, extract, tea, and/or other galenical preparation prepared from one or more plant products, containing caffeine.

3. The method of claim 1, wherein the aqueous nasal composition is sterile.

4. The method of claim 1, wherein the aqueous nasal composition further comprises a buffer and/or a saccharide.

5. The method of claim 1, wherein the aqueous nasal composition is administered as needed daily, and over a period of more than about 5 days.

6. The method of claim 1, wherein the aqueous nasal composition is administered about every 2-6 hours as needed.

7. The method of claim 1, wherein the aqueous nasal composition is delivered by a nasal spray configured to administer about 25 µL to about 150 µL of the aqueous nasal composition per activation.

8. The method of claim 1, wherein the aqueous nasal composition is delivered as doses consisting of one or more drops of the aqueous nasal composition by a unit dose device or container for nasal administration, in a total volume of about 25 µL to about 150 µL per administration.

9. The method of claim 1, wherein the aqueous nasal composition is delivered as a nasal wash or irrigation in a volume of greater than 250 µL per administration.

10. The method of claim 1, wherein the aqueous nasal composition is within 10% of isotonic to normal fluids of human nasal passages.

11. The method of claim 1, wherein the aqueous nasal composition comprises:
    from 0.0075% (w/v) to 0.075% (w/v) potassium chloride (KCl); and
    from 0.0074% (w/v) to 0.10% (w/v) calcium chloride ($CaCl_2.2H_2O$).

12. The method of claim 1, wherein in the aqueous nasal composition the total concentration of caffeine is from 0.001% (w/v) to 0.2% (w/v).

13. The method of claim 1, wherein the aqueous nasal composition comprises:
    from 0.47% (w/v) to 1.17% (w/v) sodium chloride (NaCl);
    from 0.0075% (w/v) to 0.075% (w/v) potassium chloride (KCl); and
    from 0.0074% (w/v) to 0.10% (w/v) calcium chloride ($CaCl_2.2H_2O$).

14. A method for the treatment of a human subject in need of nasal cleansing, or suffering from nasal congestion or common cold, or for the prevention of nasal infectious diseases or nasal allergic diseases, the method comprising:
    administering to the nose of the human subject an aqueous nasal composition comprising:
        a total concentration of caffeine from 0.001% (w/v) to 0.3% (w/v);
        an aqueous carrier having a pH from about 6 to about 8, the aqueous carrier comprising sodium ions from a physiologically acceptable sodium salt, potassium ions from a physiologically acceptable potassium salt, and calcium ions from a physiologically acceptable calcium salt,
        wherein the aqueous nasal composition is isotonic, hypertonic, or hypotonic to normal fluids of human nasal passages, and wherein the aqueous nasal composition comprises:
            from 0.47% (w/v) to 1.17% (w/v) sodium chloride (NaCl);
            from 0.0075% (w/v) to 0.075% (w/v) potassium chloride (KCl); and
            from 0.0074% (w/v) to 0.10% (w/v) calcium chloride ($CaCl_2.2H_2O$).

15. The method of claim 14, wherein the aqueous nasal composition comprises an aqueous infusion, extract, tea, and/or other galenical preparation prepared from one or more plant products, containing caffeine.

16. The method of claim 14, wherein the aqueous nasal composition is delivered by a nasal spray configured to administer about 25 µL to about 150 µL of the aqueous nasal composition per activation.

17. The method of claim 14, wherein the aqueous nasal composition is delivered as doses consisting of one or more drops of the aqueous nasal composition by a unit dose device or container for nasal administration, in a total volume of about 25 µL to about 150 µL per administration.

18. The method of claim 14, wherein the aqueous nasal composition is delivered as a nasal wash or irrigation in a volume of greater than 250 µL per administration.

19. The method of claim 14, wherein the aqueous nasal composition is within 10% of isotonic to normal fluids of human nasal passages.

20. The method of claim 14, wherein in the aqueous nasal composition the total concentration of caffeine is from 0.001% (w/v) to 0.2% (w/v).

* * * * *